United States Patent [19]

New, Jr. et al.

[11] Patent Number: 4,770,179

[45] Date of Patent: * Sep. 13, 1988

[54] CALIBRATED OPTICAL OXIMETER PROBE

[75] Inventors: William New, Jr., Woodside; James E. Corenman, Alameda, both of Calif.

[73] Assignee: Nellcor Incorporated, Hayward, Calif.

[ * ] Notice: The portion of the term of this patent subsequent to Nov. 11, 2003 has been disclaimed.

[21] Appl. No.: 110,373

[22] Filed: Oct. 19, 1987

Related U.S. Application Data

[63] Continuation of Ser. No. 911,978, Sep. 26, 1986, Pat. No. 4,700,708, which is a continuation of Ser. No. 827,478, Feb. 5, 1986, Pat. No. 4,621,643, which is a continuation of Ser. No. 695,402, Jan. 24, 1985, abandoned, which is a continuation of Ser. No. 414,176, Sep. 2, 1982, abandoned.

[51] Int. Cl.$^4$ .................................................. A61B 5/00
[52] U.S. Cl. .................................. 128/633; 128/664; 128/666; 356/41; 250/252.1
[58] Field of Search ............... 128/633, 634, 664, 666; 73/1 R; 356/39–42; 250/252.1

[56] References Cited

U.S. PATENT DOCUMENTS

| | | | |
|---|---|---|---|
| 2,706,927 | 4/1955 | Wood | 88/14 |
| 2,951,200 | 8/1960 | Critchlow | 324/57 |
| 3,439,258 | 4/1969 | Van Leeuwen | 323/75 |
| 3,531,978 | 10/1970 | Yeager | 73/4 |
| 3,535,637 | 10/1970 | Goransson | 324/130 |
| 3,638,640 | 2/1972 | Shaw | 128/2 R |
| 3,704,706 | 12/1972 | Herczfeld | 128/2 R |
| 3,720,199 | 3/1973 | Rishton et al. | 128/1 D |
| 3,740,533 | 6/1973 | Van Zeggelaar | 235/151.3 |
| 3,757,217 | 9/1973 | Pearson | 324/151 R |
| 3,819,276 | 6/1974 | Kiess et al. | 356/184 |
| 3,833,864 | 9/1974 | Kiess et al. | 356/184 |
| 3,847,483 | 11/1974 | Shaw et al. | 356/41 |
| 3,880,006 | 4/1975 | Poduje | 73/362 AR |
| 3,905,229 | 9/1975 | Togo et al. | 73/194 E |
| 3,910,701 | 10/1975 | Henderson et al. | 356/39 |
| 3,943,440 | 3/1976 | Edwards | 324/95 |
| 3,976,150 | 8/1976 | Wilson et al. | 177/16 |

(List continued on next page.)

FOREIGN PATENT DOCUMENTS 3100610 7/1982 Fed. Rep. of Germany .
1589461 5/1970 France .

OTHER PUBLICATIONS

Grover, Conf. Proceed. of the 26th Annual Conf. on Engr. in Med. and Biol., Minn., Minn., Sep. 20–Oct. 4, 1973 (cl. 128/633).

Schlibi et al., IEEE Trans. of Biomed. Engr., vol. BME-25, No. 1 (Jan. 1978), pp. 94–96 (cl. 128/633).

Yee et al., IEEE Trans. Biomed. Engr., vol. BME-24, No. 2, Mar. 1977, pp. 195–197 (cl. 128/633).

Merrick et al., "Continuous, Non-Invasive Measurements of Arterial Blood Oxygen Levels", *Hewlett-Packard Journal*, Oct. 1976, pp. 2–9.

*Primary Examiner*—Lee S. Cohen
*Assistant Examiner*—John C. Hanley
*Attorney, Agent, or Firm*—Thomas L. Giannetti; Jeffrey H. Ingerman

[57] ABSTRACT

A probe apparatus for use with an optical oximeter is disclosed. A pair of light emitting diodes emit light of known narrow wavelengths through an appendage of a patient onto a photosensor. A resistor of coded known resistance is used to enable the oximeter to calculate the co-efficient of extinction of the wavelengths of the LEDs. The resistor, LEDs and photosensor are mounted on self-attaching hook and eye tape for mounting the probe onto the appendage of the patient. The probe is detachably wired to the oximeter, rendering the probe completely disposable. The oximeter is programmed at the factory to calculate the co-efficients of extinction of any LEDs which may be encountered in a series of disposable probes. From the co-efficients of extinction, the pulse rate and degree of arterial oxygen saturation is computed and displayed by the oximeter.

4 Claims, 4 Drawing Sheets

U.S. PATENT DOCUMENTS

| | | | |
|---|---|---|---|
| 3,998,550 | 12/1976 | Konishi et al. | 356/39 |
| 4,000,643 | 1/1977 | Pearson | 73/88.5 R |
| 4,038,532 | 7/1977 | Burris et al. | 235/151.3 |
| 4,059,991 | 11/1977 | Dybel et al. | 73/88.5 R |
| 4,064,396 | 12/1977 | Panarello | 364/573 |
| 4,082,998 | 4/1978 | Marriott | 324/99 D |
| 4,086,915 | 5/1978 | Kofsky et al. | 128/2 L |
| 4,167,331 | 9/1979 | Nielsen | 356/39 |
| 4,179,745 | 12/1979 | Wuertele | 364/571 |
| 4,192,005 | 3/1980 | Kurtz | 364/571 |
| 4,218,916 | 8/1980 | Mutziger | 73/359 R |
| 4,225,410 | 9/1980 | Pace | 204/195 R |
| 4,236,935 | 12/1982 | Clark, III | 378/48 |
| 4,263,803 | 4/1981 | Burkhardt | 73/1 R |
| 4,266,554 | 5/1981 | Hamaguri | 128/633 |
| 4,282,578 | 8/1981 | Payne et al. | 364/573 |
| 4,290,297 | 9/1981 | Anderson | 73/1 R |
| 4,323,972 | 4/1982 | Winter | 364/482 |
| 4,331,026 | 5/1982 | Howard et al. | 73/81 |
| 4,337,638 | 6/1982 | Leonard et al. | 73/1 R |
| 4,349,886 | 9/1982 | Ibar | 364/573 |
| 4,407,272 | 10/1983 | Yamaguchi | 128/6 |
| 4,407,290 | 10/1983 | Wilber | 128/633 |
| 4,407,298 | 10/1983 | Lentz et al. | 128/713 |
| 4,446,715 | 5/1984 | Bailey | 73/1 R |
| 4,481,804 | 11/1984 | Eberhard et al. | 73/1 G |
| 4,494,550 | 1/1985 | Blazek et al. | 128/664 |
| 4,621,643 | 11/1986 | New, Jr. et al. | 128/633 |

CALIBRATED OPTICAL OXIMETER PROBE

CROSS-REFERENCE TO RELATED APPLICATIONS

This application is a continuation of copending U.S. patent application Ser. No. 911,978, filed Sept. 26, 1986, now U.S. Pat. No. 4,700,708, which is a continuation of U.S. patent application Ser. No. 827,478, filed Feb. 5, 1986, now U.S. Pat. No. 4,621,643, which was a continuation of U.S. patent application Ser. No. 695,402, filed Jan. 24, 1985, now abandoned, which was a continuation of U.S. patent application Ser. No. 414,176, filed Sept. 2, 1982, now abandoned.

FIELD OF THE INVENTION

This invention relates to solid state monitors for photoelectric determination of arterial oxygen saturation and of pulse rate in a human or animal patient, more particularly to a disposable probe calibrated through a remote sensing apparatus including a transducer herein called an information encoding component.

BACKGROUND OF THE INVENTION

A serious problem exists in operating rooms. Specifically, the chemical determination of oxygen level in blood consumes at least 3 to 5 minutes. A patient deprived of blood oxygen for such a duration typically incurs irreversible brain damage if not death.

U.S. Pat. No. 2,706,927 to Wood disclosed the computation of oxygen saturation from measurements of light adsorption of body tissue at two wavelengths. A series of devices and procedures have been founded using this technology.

A required peripheral device of such photoelectric oximeters is a photoelectric probe. Typically, such a probe is clamped to an appendage of a patient's body, such as an ear or a finger. Such probes require at least one light source for directing light into the appendage and at least one sensor for receiving light diffused out of the appendage. One method of obtaining light of the desired frequency has been to use a light source of indeterminate wavelength range in combination with a monochromatic filter of known output. Such devices are inefficient, and result in unwanted power demands and heat generation.

U.S. Pat. No. 3,704,706 to Herczfeld et al. disclosed the use of a solid state red laser in an optical probe with a solid stsate photodetector. Although lasers are useful for emitting monochromatic light of known wavelength, thereby eliminating need for a filter, they remain expensive and unwieldy.

U.S. Pat. No. 3,847,483 to Shaw et al. disclosed the use of light emitting diodes to provide the necessary monochromatic light. The probe of Shaw required expensive fiber optic cables.

A problem with all prior art devices is that they are too expensive to be readily disposable. The need for a truly disposable probe is great, given the many surgical applications in which sterility must be assured. The prior art optical probes, being more or less permanent portions of their respective oximeters, were subjected to a one time determination of the wavelength of the light sources therein and the oximeter was then programmed or adjusted to process light of the known wavelength.

A problem in developing disposable probes, therefore, has been the necessity to avoid having to reprogram or adjust the oximeter for each new probe or alternately to maintain probes within narrow limits of wavelength variation, a clearly impractical task.

Re-calibration, perhaps necessitating return of the oximeters to the factory, can become necessary even for prior art devices when, for example, a probe is broken. Alternatively, a supply of light sources having consistently identical wavelengths is required. In particular, light emitting diodes are known to vary in wavelengths from unit-to-unit.

Other optical probes are shown in patents to Shaw, U.S. Pat. No. 3,638,640, Neilsen, U.S. Pat. No. 4,167,331, and Konishi, U.S. Pat. No. 3,998,550.

SUMMARY OF THE INVENTION

The present invention provides an optical oximeter probe which includes at least one narrow bandwidth light emitting diode and at least one photoelectric sensor. An information encoding component such as a resistor of known resistance is selected to correspond to the measured wavelength of the LED and is provided with each probe. The elements are mounted on a flexible fastening medium. The wires from the electrical elements terminate at a connector for detachably connecting the probe to the related oximeter. Coding in other manners, such as the wiring of a multiconductor plug in a digital valve or binary array or into a disposable memory containing the color information is disclosed.

The primary object of this invention is to provide apparatus for directing light onto a portion of a human body for the detection of oxygenated blood flow which is inexpensive, replaceable, easily applied and which overcomes the disadvantages and limitations of the prior art.

It is a further object of this invention to provide an optical probe whose wavelength emission characteristics are readily ascertainable by the attendant oximeter.

Another object of this invention is to enable factory calibration of LEDs for use in such probes. Typically, LEDs are purchased in batches of one general wavelength, but those exact wavelength characteristics are unknown and vary from piece to piece.

It is a further object of this invention to eliminate the necessity for oximeters to be calibrated for new probes, other than the initial factory calibration.

Yet another object of this invention is to provide flexible attachment means for the probe which will allow rapid attachment to human or animal appendages of varying sizes yet maintain the photoelectric sensor in direct optical isolation from the LEDs.

Yet another object of this invention is to disclose wiring of a multiconductor plug in a binary array to transmit probe calibration.

DESCRIPTION OF THE PREFERRED EMBODIMENTS

Figure 6:
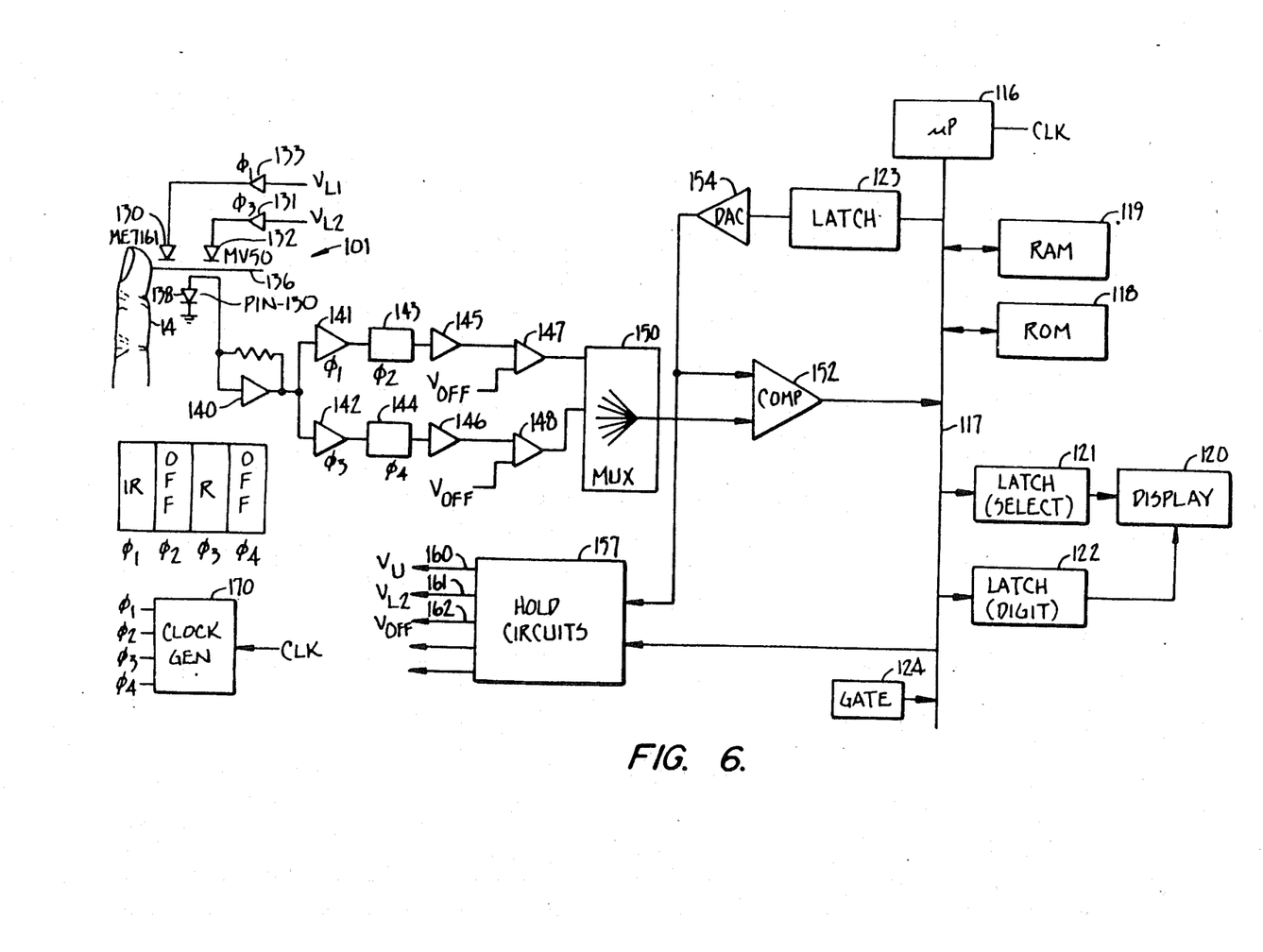
FIG. 6 is a circuit schematic of an oximeter utilizing the calibrated probe of this invention.

Referring to FIG. 6, the pulse oximeter of this invention is illustrated.

Conventional microprocessor 116 has a bus 117 extending therefrom. Bus 117 has connected thereto conventional ROM 118 and RAM 119. An LED display 120 is schematically illustrated having a select latch 121 and a digit designation latch 122.

Having set forth the more or less conventional portions of the microprocessor, attention will now be directed to the analog portions of the circuitry.

Finger 14 of a patient is illustrated with probe 101 having schematic detection circuitry. First light emitting diode 132 in the red range and a second light emitting diode 130 in the infrared range are sequentially pulsed to emit light in their respective frequencies by amplifiers 131, 133. Typically, LED 132 is in the 660 nanometer range with LED 130 being in the 940 nanometer range.

It is necessary that maximum light from the active light emitting diode go through the flesh in finger 14. Therefore, a light impervious barrier 136 is placed between photosensor 138 and the paths to the light emitting diodes 130 and 132 which are not through finger 14. Barrier 136, terminating in contact with the flesh of finger 14, makes the path between the respective light emitting diodes 130, 312 and the light receiving diode 138 occur only through the flesh of finger 14.

Signal received from each respective light emitting diode first passes through a pre-amplifier 140. This signal is thereafter amplified in parallel at amplifiers 141, 142. As amplified, the signal is passed in parallel from each amplifier through respective phase detectors 143, 144. Passage through respective low pass filters 145, 146 thereafter occurs. Amplification at offset amplifiers 147, 148 then takes place. The pulsatile component is passed to multiplexer 150.

Multiplexer 150 has output to a comparator 152. Comparator 152 is ramped in half steps by a 12 bit digital to analog converter (hereinafter DAC) 154. DAC 154 places a comparison signal divided in one part from 4096 parts with the comparator outputting to bus 117.

The reader will recognize that not all human fingers and appendages are the same. Specifically, the difference between the races, skin pigment, weight, age, maturity and other factors all can lead to different signals being sensed at photosensor 138, even though the frequency and intensity of the light signal output at each of the diodes 130, 132 is the same.

Accordingly, microprocessor 116 is programmed to receive a signal from photosensor 138 within an optimum range. Utilizing a second operating phase of DAC 154, and communicating a signal to a sample hold 157, the individual LED's 130, 132 are given voltage outputs 160, 161. These voltage outputs 160, 161 are adjusted so that in each case photosensor 138 looks at a signal well within the range of the DAC.

Clock 170 controls the sequential output of light from the light emitting diodes 130, 132 to a duty cycle of at least 1 in 4. This is schematically illustrated by signals $\phi1$ through $\phi4$. Reception of signal at detector 143 occurs during time periods $\phi1$ and $\phi2$ and reception of signal occurs at detector 144 during time periods $\phi3$ and $\phi4$.

It can be immediately realized that during respective time periods $\phi1$, $\phi3$ active signal from the light emitting diodes 130, 132 is being received. During the time periods $\phi2$ and $\phi4$, no signal and only noise is being received. As will hereinafter become apparent, by amplifying the negative signal before passage through the low pass filter, noise can be subtracted out utilizing the illustrated 1 in 4 duty cycle.

Applicants herewith incorporate by reference their U.S. application entitled "Pulse Oximeter," U.S. patent application Ser. No. 414,174, filed Sept. 2, 1982, abandoned in favor of U.S. patent application Ser. No. 417,311, filed Sept. 13, 1982 now abandoned. FIG. 6 is a copy of the FIG. 2 from that application.

The Summary of Invention in the incorporated application is:

SUMMARY OF INVENTION

A pulse oximeter is disclosed of the type wherein light of two different wavelengths is passed through any human or animal body pulsatile tissue bed, such as a finger, an ear, the nasal septum or the scalp, so as to be modulated by the pulsatile component of arterial blood therein, and thereby allowing indication of oxygen saturation, blood perfusion and heart rate. The level of incident light is continually adjusted for optimal detection of the pulsatile component, while permitting accommodation to variable attenuations due to skin color, flesh thickness and other invariants. At significant slope reversal of the pulsatile component to negative (indicating a wave maximum), wave form analysis of blood flow occurs. A quotient of the pulsatile component of light transmission over the constant component of light transmission is measured for each of two wavelengths by direct digital tracking. The respective quotients are thereafter converted to a ratio, which ratio may be thereafter fitted to a curve of independently derived of oxygen saturation for the purpose of calibration. The saturation versus ratio calibration curve may be characterized by various mathematical techniques including polynomial expansion whereby the coefficients of the polynomial specify the curve. An output of pulse rate, pulsatile flow and oxygen saturation is given. An incident light source duty cycle is chosen to be at least 1 in 4 so that noise, inevitably present in the signal, may be substantially eliminated and filtered.

A representative claim is:

A pulse oximeter for determining arterial oxygen saturation and arterial pulse amplitude in a patient, said oximeter comprising: first and second light emitting sources for emitting sequential light pulses in the red and infrared into the flesh of a human; a sensor sensitive to each of said light sources having an indirect light path through the flesh of said human from said first and second light sources; said sensor sequentially outputting signals to an amplifier from each of said light sources; means for digitally tracking the light absorption; means for dividing the change of light transmission due to the pulsatile component of blood flow with respect to the total light transmission to determine a quotient of light absorption for each optical wavelength; means for making a ratio related directly to the respective quotients of light transmission at each said frequency and means for fitting the ratios of light transmission to experimentally determined saturations at said ratio to enable the optical determination of saturation.

Figures 1, 2, 3:
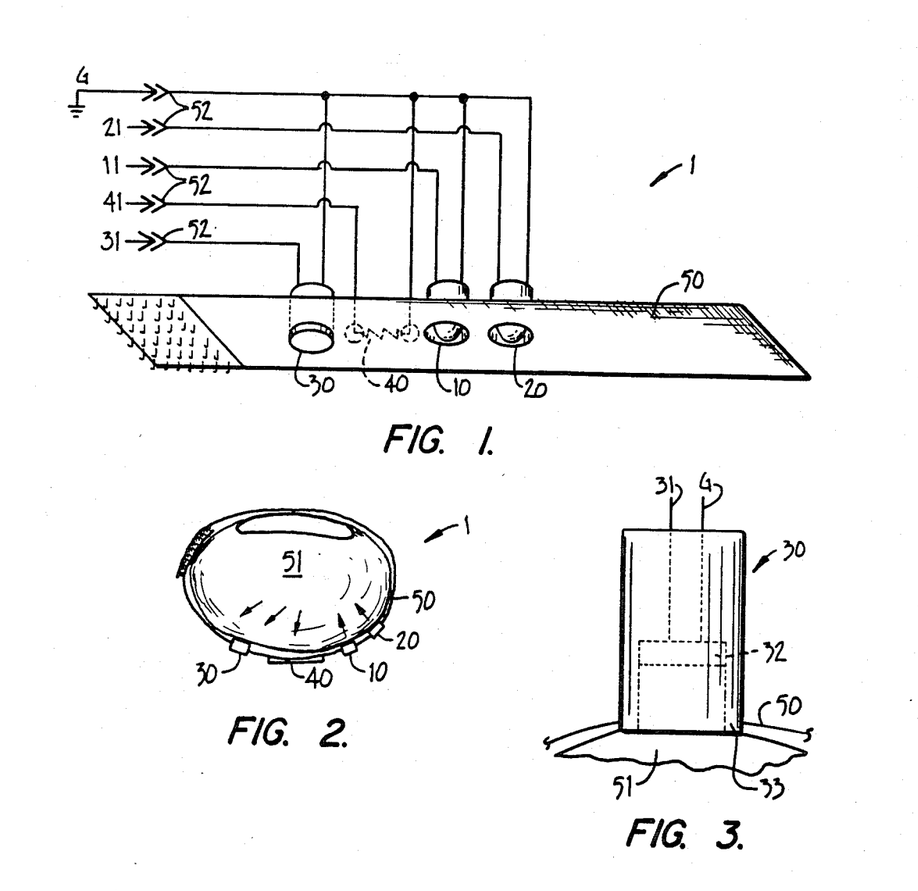
FIG. 1 is a part perspective, part schematic diagram of the optical probe of the preferred embodiment of the present invention.
FIG. 2 is an end view of a patient's finger showing placement of the probe of the present invention.
FIG. 3 is a side elevation of an embodiment of a photoelectric sensor of the probe.

Referring to FIG. 1, a part-schematic, part-perspective view of the optical probe 1 is shown. A suitable length of adjustable, self-fastening tape 50 is provided, such as that sold under the trademark VELCRO, obtainable from American Velcro, Inc. Incorporated into tape 50 at suitably spaced intervals are the electrical components of probe 1. Photoelectric sensor 30 is attached to the outside of tape 50 and protrudes slightly from the underside of tape 50. Sensor 30 has ground wire G and lead wire 31. Light emitting diode 10, typically emitting frequencies in the infrared range of the spectrum, is mounted to and pierces tape 50 in a similar manner to sensor 30 and at a distance from sensor 30 selected upon the basis of the typical appendage size expected to be encountered. LED 10 is connected to ground wire G and has input lead wire 11. Placed in proximity to LED 10 is a second LED 20, typically having wavelength emission characteristics in the red range of the spectrum. LED 20 attaches to ground wire G and has input lead wire 21.

Resistor 40 is shown mounted to tape 50 between sensor 30 and LED 10. However, the physical location of resistor 40 is not important and it may be mounted to probe 1 at any other convenient location. Resistor 40 has input lead wire 41 and is connected to ground wire G.

Figure 4:
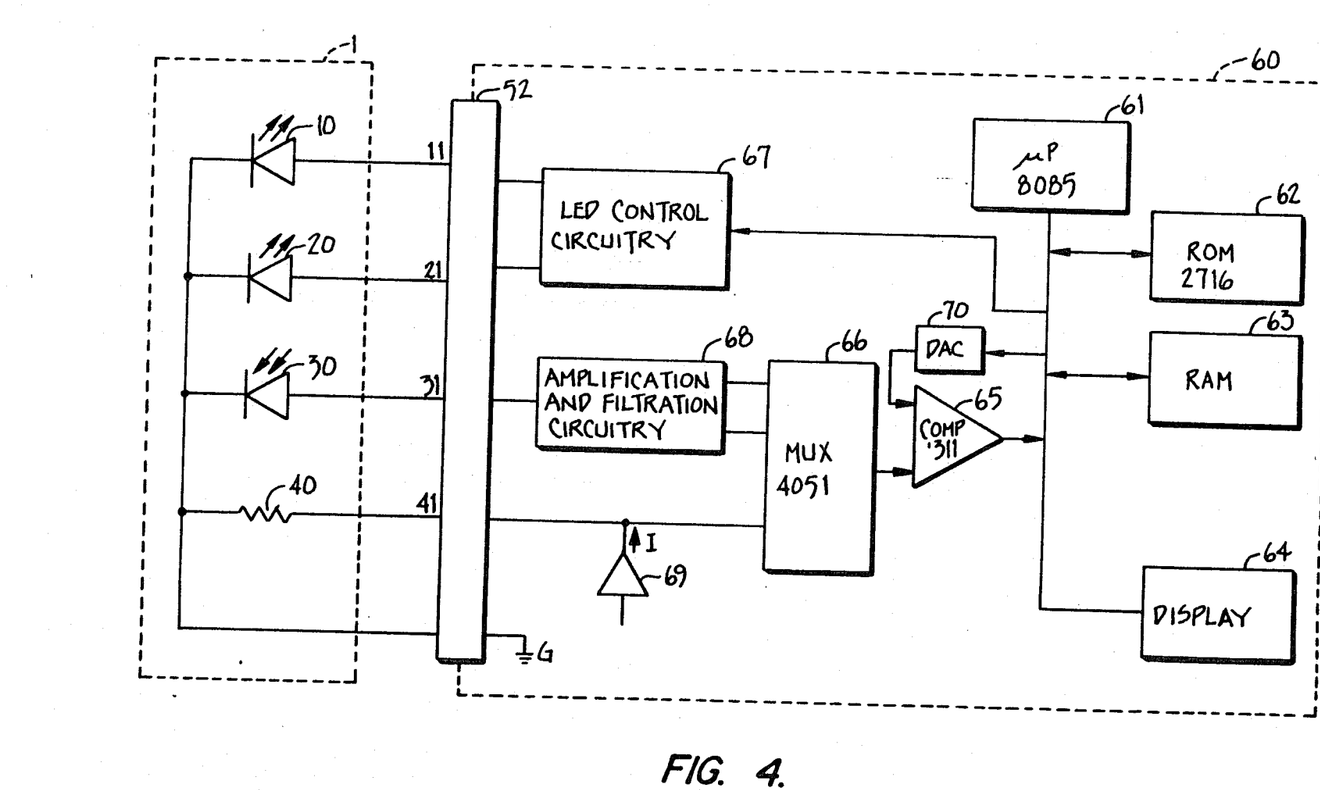
FIG. 4 is a simplified schematic circuit diagram illustrating the method in which an oximeter microprocessor decodes the wavelength value of the probe through use of a coded resistor.

Wires G, 11, 21, 31, 41 lead to connector 52 so that probe 11 may be readily disconnected from the oximeter 60 (schematically illustrated in FIG. 4).

The probe 1 illustrated in FIG. 1 is designed for use in connection with an oximeter 60 designed to operate in conjunction with two LEDs 10, 20 sequentially transmitting light to a single sensor 30. However, the mechanism of the instant invention works equally well for oximeters requiring only a single LED and single or multiple photo sensors. Oximeters requiring more than two LEDs may be equally well accommodated by the probe of the present invention.

FIG. 2 is an end elevation of a typical finger 51 of a human patient. Finger 51 is encircled by probe 1 at its tip by overlapping the ends of self-connecting tape 50. Light emitted from LEDs 10, 20 enter the flesh of finger 51 and are subjected to diffusion and scattering. Sensor 30 picks up only light which has been diffused through the flesh of finger 51.

FIG. 3 is a detailed side elevation of sensor 30, showing the manner in which it is assured that no light emitted by LEDs 10, 20 is received by sensor 30 without first passing through finger 51. Sensor element 32 is recessed somewhat within metal cylinder wall 33 of the sensor housing. Since tape 50 presses sensor 30 directly against the skin of finger 51, it is readily seen that no light passes to sensor element 32 other than through the flesh of finger 51.

Probe 1 is constructed in the following manner: LED's 10, 20 are selected from batches of LEDs with generally known wavelength characteristics. The exact wavelength characteristics of the specific LED's 10, 20 chosen are determined at this time through readily available metering means. Resistor 40 or a similar impedance reference is then selected to have an impedance or specifically a resistance whose amount is exactly specified by a table made available to the factory technician for this purpose, of all possible wavelength combinations which may be expected to be encountered from the available supplies of LEDs. The following table is an example of how a single resistor 40 might be selected for any hypothetical combination of LED's 10, 20 in a case where each has only two possible wavelengths:

TABLE A

| Resistor 40 | LED 10 | LED 20 |
| --- | --- | --- |
| 150 ohms | 940 nM | 660 nM |
| 160 ohms | 950 nM | 660 nM |
| 170 ohms | 940 nM | 670 nM |
| 180 ohms | 950 nM | 670 nM |

A typical probe will have an infrared LED 10 of wavelength 940 nanometers and a red LED 20 of wavelength 660 nanometers. According to the above table, a probe having such wavelength characteristics will be supplied at the factory with a resistor 40 of one, and only one, resistance value, in this case shown to be 150 ohms.

The value in having such a unique known resistance incorporated into probe 1 is shown by reference to FIG. 4. Oximeter 60 contains a microprocessor 61, and a read only memory 62 and random access memory 63. Table A (the same table used for calibrating probe 1 at the factory) no matter how extensive, may be easily programmed into ROM 62 at the time oximeter 60 is fabricated. Current I from current source 69 is passed through resistor 40. The resulting voltage (per Ohm's law) is passed through multiplexor 66 through comparator 65, to microprocessor 61.

Microprocessor 61 may be programmed to calculate the resistance of resistor 40 and thereafter to look up the wavelengths of LED's 10, 20 from Table A in ROM 62. Microprocessor 61 is also programmed to itself recalibrate the optical comparison circuitry of oximeter 60 once the wavelengths of LEDs 10, 20 are known. By this means, it is not required to recalibrate by hand oximeter 60 for each new probe 1 nor, alternatively, to require that LED's 10, 20 be of precisely standardized wavelengths.

The specific function and design of the circuitry schematically illustrated in FIG. 4 is seen as obvious when taken in combination with the general description and read only memories are well known and understood and it is well within the capability of a person with ordinary skill in the art to design and program microprocessor 61 to calculate the resistance of resistor 40 and thereby obtain the wavelengths of LEDs 10, 20 from a simple lookup table in a ROM 62.

Probe 1 may be used with any number of prior art oximeters, the method of operation of which is well understood and beyond the scope of the teaching of the present invention. Basically, for each heart beat, fresh arterial blood is pumped into the capillaries of finger 51, thereby causing a periodic increase and decrease in light intensity observed by sensor 30. The oxygen saturation of hemoglobin in the pulsatile blood may be determined by the oximeter 60. For any known wavelength, there is a known extinction coefficient B. Given B and measuring the intensity of diffused light received by sensor 30 the oxygen saturation can be computed and displayed. In fact, the coefficients B of the various wavelengths of table A can be substituted for the wavelengths directly when the table is programmed into ROM 62, thereby eliminating a computational step.

Microprocessor 61, through LED control circuitry 67, operates LEDs 10, 20. Light from LEDs 10, 20 results in current in sensor 30 which passes through amplification and filtration circuitry 68 to multiplexor 66. Comparator 65 and a digital to analog converter 70 are operative as an analog to digital converter means to present a digital signal to the microprocessor 61, thereby allowing microprocessor 61 to determine oxygen saturation and/or pulse rate. Results are shown on display 64.

Figure 5:
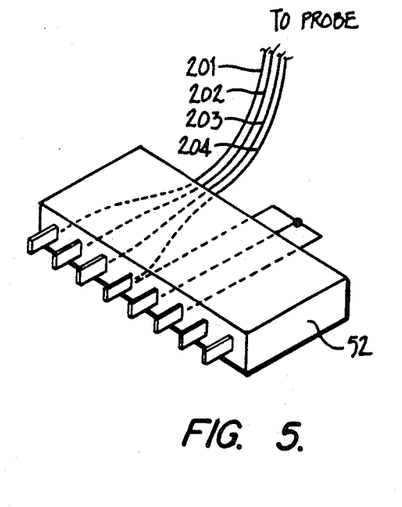
FIG. 5 is a schematic of the probe of this invention calibrated by a multiconductor plug and wired in a binary array.

Referring to FIG. 5, an alternate way of coding a probe of this invention is illustrated. Specifically, an eight pin connector 52 similar to the connector 52 of FIG. 4 is illustrated having respectively lead lines 201, 202, 203 respectively communicating to light emitting diode 130, light emitting diode 132 and photodetector 138. Conductor 204 is illustrated providing the ground connection.

It will be noted that the eight pin connector 52 of FIG. 5 has four empty channels. These channels can be provided to communicate the coded value of the probe.

For example, assuming that the connectors when provided with a common potential provide a true binary value and when independent of any potential (i.e., a high impedance or open circuit) provide a false binary value. Thus, the four conductors of plug 52, as illustrated in FIG. 5, would communicate the binary value 1100. Thus, communication of the resistance value of the connected probe would be possible by coding the connector to a value of 1 part in 16.

Those skilled in the art will appreciate that other binary connections could as well be made. For example, by expanding the number of connectors on the probe relatively large expansions can occur.

Those skilled in the art will realize that in determining the variable transmission of light in human flesh the frequency at which the flesh is integrated by a substantially monochromatic light source is critical. If the frequency varies the results of the instrument can be inaccurate with such variation. Simply stated, at different points in the spectral frequency, oxygenated hemoglobin and reduced hemoglobin transmit varying amounts of light.

Commercially produced light emitting diodes do have variation in their spectral frequency from diode to diode. Therefore if such commercially produced diodes are going to be used as replaceable probes in an instrument it has been found that provision must be made for a probe by probe calibration of the instrument. Thus, effectively disposable probes can be readily used even though they are affecting integration at differing frequencies from probe to probe.

Some comment can be made directed specifically at calibrating the disposable probe of the instrument herein. As a practical matter, the blood of a human is interrogated through the skin by light transmission utilizing red and infrared. The rate of change of constants in the frequency of the infrared diode has little effect.

Not so in the red range. It has been found that the attenuation of light in oxygenated and unoxygenated hemoglobin has a rapidly changing slope in the red range. This being the case, it is of primary concern to calibrate in the particular instrument illustrated in the red range.

Those skilled in the art will realize that there are many ways in which change of instrument calibration can occur. Specifically, separate look-up tables can be generated for various grouped relationships. Alternately, and perhaps more productively, incremental alternation to the constants of curvature between the saturation level S and the ratio of quotients R of light transmission can be determined.

Although the foregoing invention is described in some detail by way of illustration and example for purpose of clarity of understanding, it is understood that certain changes and modifications may be practiced and equivalents employed within the spirit of the invention as limited only by the scope of the appended claims. For example, two resistors may be used in place of one, each resistor coded to the wavelength of a separate LED. Other components could be used in place of resistors, e.g., capacitors or the like. Therefore, the above description and illustrations should not be construed as limiting the scope of the invention which is defined by the appended claims.

What is claimed is:

1. An oximeter for use with a probe having a first light emitting means emitting light having a first known wavelength value, means for sensing the light emitted by said first light emitting means and for generating a signal representative of the light sensed, means for detachably wiring the probe to the oximeter and for providing communication of electrical signals between the probe and the oximeter including said signal representative of the light sensed, and encoding means for providing first encoded signals to the oximeter which are indicative of the known wavelength value of said first light emitting means, said oximeter comprising:
    processing means for operating on said signal representative of the light sensed, using appropriate coefficients, for determining oxygen saturation; and
    decoding means responsive to said first encoded signals for selecting said appropriate coefficients based upon the known wavelength of the first light emitting means.

2. The oximeter of claim 1 for use with a probe additionally having a second light emitting means emitting light having a second known wavelength value, said light sensing means also sensing light emitted by said second light emitting means, said encoding means further comprising means for providing second encoded signals to the oximeter indicative of the known wavelength value of the light emitted by the second light emitting means, wherein:
    said decoding means is further responsive to said second encoded signals for selecting coefficients based upon the known wavelength of said second light emitting means.

3. The oximeter of claim 1 wherein said decoding means comprises a programmed microprocessor.

4. The oximeter of claim 1 further comprising means for passing a current through an impedance element in said encoding means, wherein said encoded signals are voltage signals produced by passing said current through said impedance element.

* * * * *

UNITED STATES PATENT AND TRADEMARK OFFICE
CERTIFICATE OF CORRECTION

PATENT NO.  : 4,770,179

DATED       : September 13, 1988

INVENTOR(S) : William New, Jr. et al.

It is certified that error appears in the above-identified patent and that said Letters Patent is hereby corrected as shown below:

Column 2, line 43, "those" should be -- whose --.

Column 3, line 34, "312" should be -- 132 --.

Column 6, line 42, after "description" should be inserted -- of its function.  The functions of microprocessors --.

Column 7, line 53, after "constants" should be inserted -- in the infrared is relatively flat.  Therefore a variance --.

Signed and Sealed this

Twenty-third Day of April, 1991

*Attest:*

HARRY F. MANBECK, JR.

*Attesting Officer*     *Commissioner of Patents and Trademarks*